(12) United States Patent
Robb (10) Patent No.: US 11,623,121 B1
(45) Date of Patent: Apr. 11, 2023

(54) USING AGGREGATE ACTIVITY DATA TO GENERATE A GRADE ADJUSTED PACE MODEL

(71) Applicant: Strava, Inc., San Francisco, CA (US)

(72) Inventor: Drew Robb, San Francisco, CA (US)

(73) Assignee: Strava, Inc., San Francisco, CA (US)

( * ) Notice: Subject to any disclaimer, the term of this patent is extended or adjusted under 35 U.S.C. 154(b) by 829 days.

(21) Appl. No.: 16/292,969

(22) Filed: Mar. 5, 2019

Related U.S. Application Data (60) Provisional application No. 62/731,680, filed on Sep. 14, 2018.

(51) Int. Cl.

| | |
|---|---|
| *A63B 24/00* | (2006.01) |
| *A63B 71/06* | (2006.01) |
| *A61B 5/024* | (2006.01) |
| *G16H 20/30* | (2018.01) |
| *G01C 5/00* | (2006.01) |
| *A61B 5/00* | (2006.01) |
| *A61B 5/11* | (2006.01) |
| *G01C 9/02* | (2006.01) |

(52) U.S. Cl.
CPC .......... *A63B 24/0075* (2013.01); *A61B 5/024* (2013.01); *A61B 5/1112* (2013.01); *A61B 5/7203* (2013.01); *A63B 71/0686* (2013.01); *G01C 5/00* (2013.01); *G01C 9/02* (2013.01); *G16H 20/30* (2018.01); *A61B 2503/10* (2013.01); *A63B 71/0622* (2013.01); *A63B 2071/0694* (2013.01); *A63B 2220/18* (2013.01); *A63B 2220/20* (2013.01); *A63B 2220/30* (2013.01); *A63B 2220/62* (2013.01); *A63B 2220/73* (2013.01); *A63B 2230/06* (2013.01)

(58) Field of Classification Search
CPC . A63B 24/00; A63B 24/0075; A63B 71/0686; A63B 71/06; A63B 2220/18; A63B 2220/62; A63B 2220/73; A63B 2230/06; G16H 20/30; A61B 5/00; A61B 5/11; A61B 5/024; A61B 2503/10; G01C 9/02; G01C 5/00
See application file for complete search history.

(56) References Cited

U.S. PATENT DOCUMENTS

| | | | |
|---|---|---|---|
| 9,237,868 B2 * | 1/2016 | Seppanen | A61B 5/222 |
| 2011/0275940 A1 * | 11/2011 | Nims | A63B 24/0062 |
| | | | 600/483 |
| 2012/0116550 A1 * | 5/2012 | Hoffman | A63B 24/0084 |
| | | | 700/91 |
| 2016/0107066 A1 * | 4/2016 | Lee | G06Q 30/02 |
| | | | 482/3 |
| 2018/0185704 A1 * | 7/2018 | Liu | A63B 24/0021 |
| 2019/0192911 A1 * | 6/2019 | Quast | G06K 9/00348 |

OTHER PUBLICATIONS

Minetti et al., Energy Cost of Walking and Running at Extreme Uphill and Downhill Slopes, J Appl Physiol, Sep. 2002, pp. 1039-1046, vol. 93.

* cited by examiner

*Primary Examiner* — Jay Trent Liddle
*Assistant Examiner* — Alyssa N Brandley
(74) *Attorney, Agent, or Firm* — Van Pelt, Yi & James LLP (57) ABSTRACT

Using aggregate activity data to generate a grade adjusted pace model is disclosed, including: receiving a plurality of activities; selecting a portion of the plurality of activities based at least in part on recorded heart rate information associated with the plurality of activities; and generating a Grade Adjusted Pace (GAP) model based at least in part on the selected portion of the plurality of activities.

16 Claims, 9 Drawing Sheets

FIG. 9

USING AGGREGATE ACTIVITY DATA TO GENERATE A GRADE ADJUSTED PACE MODEL

CROSS REFERENCE TO OTHER APPLICATIONS

This application claims priority to U.S. Provisional Patent Application No. 62/731,680 entitled USING AGGREGATE RUNNING DATA TO FIT A GRADE ADJUSTED PACE MODEL filed Sep. 14, 2018 which is incorporated herein by reference for all purposes.

BACKGROUND OF THE INVENTION

Athletes such as runners care about measuring pace as a way to measure the intensity of a workout. Runners form associations of the difficulty of running at a given pace. Elevation changes during a run can dramatically affect the perceived difficulty of running a given horizontal distance. For example, an increase in elevation along a run can increase the difficulty of the run. However, it is desirable to adjust the pace of an athlete's run (or other physical activity across a horizontal distance) given the measured grade (e.g., elevation or gradient) (along different points) of the surface on which the athlete runs such that the adjusted pace could reflect what the athlete's pace would have been on a flat surface.

BRIEF SUMMARY OF THE INVENTION

A Grade Adjusted Pace (GAP) model is generated based on aggregated activity data. A GAP model comprises a function that maps elevation gradient values (i.e., vertical elevation change per horizontal distance) to a dimensionless grade pace adjustment coefficient that gives the relative difficulty of running some speed at that elevation gradient versus running at zero gradient (i.e., on a flat elevation). Recorded activities (e.g., recorded runs) associated with various users are received. A portion of the recorded activities is selected based at least in part on recorded heart rate information associated with the activities. Then, the GAP model is generated based at least in part on the selected portion of the recorded activities.

BRIEF DESCRIPTION OF THE DRAWINGS

Various embodiments of the invention are disclosed in the following detailed description and the accompanying drawings.

DETAILED DESCRIPTION

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

A Grade Adjusted Pace (GAP) model comprises a function that maps elevation gradient values (i.e., vertical elevation change per horizontal distance) to a dimensionless grade pace adjustment coefficient that gives the relative difficulty of running some speed at that elevation gradient versus running at zero gradient (i.e., on a flat elevation). For example, the pace adjustment coefficient value at zero gradient should be 1.0, since by definition, no correction is necessary at flat elevation. For small positive gradients, the grade pace adjustment coefficient should be larger than 1.0, since running uphill is more difficult. For small negative gradients, the grade pace adjustment coefficient should be smaller than 1.0, since running down a slight hill is easier. The uphill gradient where the grade pace adjustment coefficient is 2.0 would be expected to slow a runner down twice as much as an equivalent flat horizontal distance.

One traditional GAP model has been derived from a study and in which the GAP model is derived from physiological measurements of energy consumption of runners in a lab setting running on a treadmill at different gradients. However, this traditional GAP model tended to error on downhill race performance by as much as a factor of three. In addition, GAP models that were generated based on athletes performing in lab settings were based on a limited number of running activities.

Embodiments of using aggregate activity data to generate a Grade Adjusted Pace (GAP) model are described herein. Recorded activities (e.g., recorded runs) are received. A portion of the plurality of activities is selected based at least in part on recorded heart rate information associated with the plurality of activities. A GAP model is generated based at least in part on the selected portion of the plurality of activities.

Figure 1:
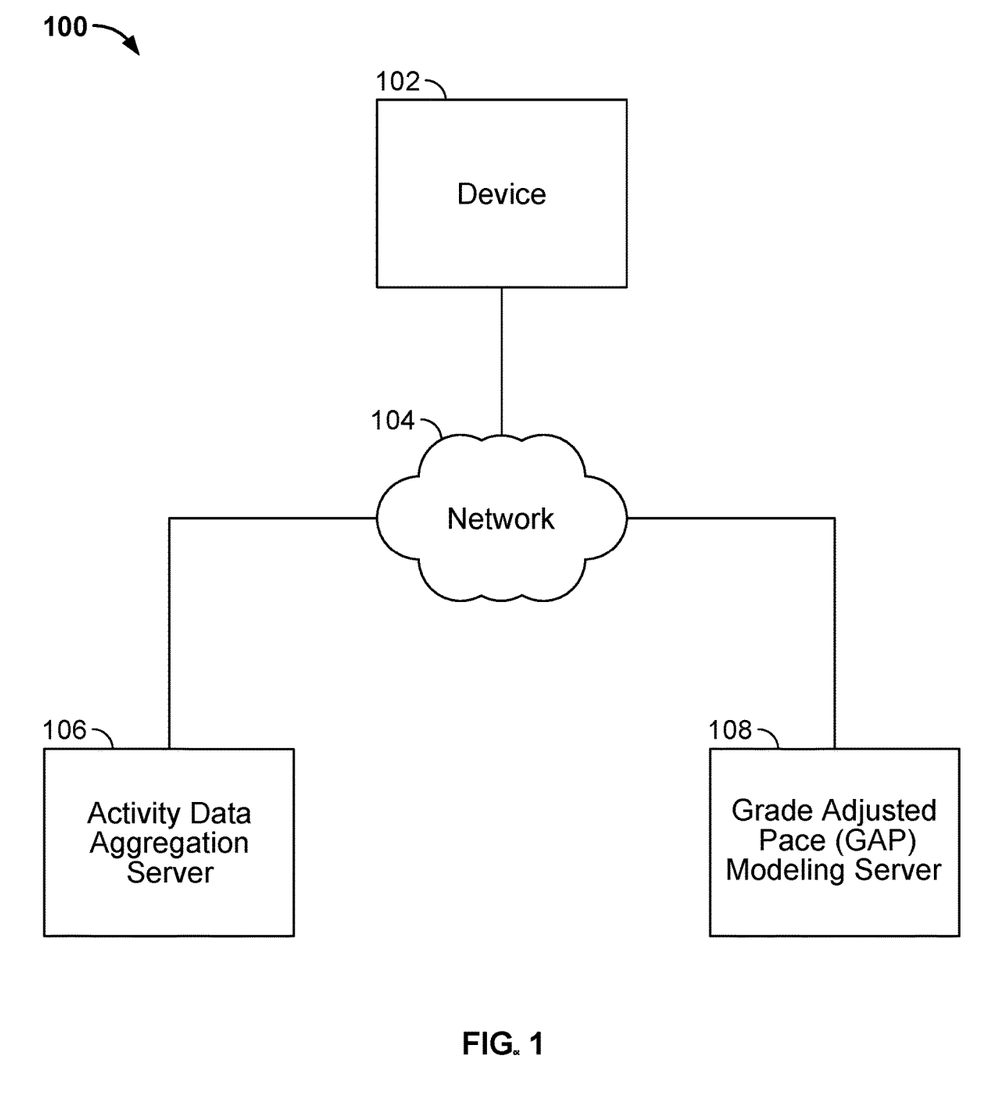
FIG. 1 is a diagram showing an embodiment of a system for using aggregate activity data to generate a GAP model in accordance with some embodiments.

FIG. 1 is a diagram showing an embodiment of a system for using aggregate activity data to generate a GAP model in accordance with some embodiments. System 100 includes device 102, network 104, activity data aggregation server 106, and grade adjusted pace (GAP) modeling server 108. Network 104 may include high-speed data networks and/or telecommunication networks.

Device 102 is a device that can record Global Positioning System (GPS) data and/or other data associated with an activity. Device 102 can also be a device to which GPS data and/or other data associated with a physical activity can be uploaded or transferred. Examples of device 102 include, but are not limited to: a GPS device (e.g., Garmin Forerunner® and Edge® devices, including Garmin Forerunner® 110, 205, 301, 305, 310XT, 405, 405CX, and Garmin Edge® 305, 605, 705, 500, 800, 810, and 1000), a mobile phone, such as a smart phone (e.g., an Android®-based device or Apple iPhone® device) including a GPS recording application (e.g., MotionX®, Endomondo®, Strava®, and RunKeeper®), a computer, a tablet device, and/or other general purpose computing devices and/or specialized computing devices, which typically include a general processor, a memory or other storage component(s), a network or input/output (I/O) capability, and possibly integrated GPS functionality or support or an interface for a GPS device or GPS functionality.

In various embodiments, device 102 (or an activity tracking application executing thereon) is configured to record GPS data and auxiliary data associated with an athletic activity during the activity. For example, auxiliary data associated with an activity may include physiological, environmental, and/or performance data. In some embodiments, device 102 is configured to receive recorded GPS data and auxiliary data associated with an activity subsequent to the completion of the activity (e.g., such information is uploaded to device 102). In various embodiments, a recorded run is a series of measurements recorded at corresponding instances/points in time during a user's running activity. For example, at each point/instance of time, one or more of the following measurements are recorded and/or computed from recorded data: current geographic (e.g., GPS) information, current time, cumulative distance, current elevation, current pace, current elevation gradient, and current heart rate.

In some embodiments, an "activity" refers to an instance of an athletic performance. Example types of an activity include cycling, running, and skiing. In some embodiments, GPS data includes a series of consecutive and discrete GPS data points (e.g., latitude and longitude coordinates sometimes referred to as "Lat-Lng Data") with a timestamp for each GPS data point. In some embodiments, auxiliary data includes, but is not limited to, barometric data (e.g., elevation/gradient data), heart rate, power/watts (e.g., energy expended), time, speed (e.g., mean and/or maximum speed per segment and/or route, in which mean speed, for example, can be derived from time and GPS information), and/or cadence. Auxiliary data can be recorded at various granularities. For example, auxiliary data can correspond to each GPS data point, the entire activity (e.g., the auxiliary data includes means of the metrics), and/or portions of the activity. As an example, one can use device 102 on a bike ride. At the end of the bike ride, the athlete can review his performance with the recorded GPS data (e.g., through a user interface of device 102) to observe the geographical track (e.g., the set of GPS points) that he traversed, how much energy he expended along the ride, how fast he finished it in, mean speed, elevation-based metrics, and/or other metrics. In some embodiments, device 102 is configured to store the recorded GPS data and the auxiliary data and/or send the recorded data associated with an athletic activity to activity data aggregation server 106. In some embodiments, device 102 is configured to send the recorded data associated with an activity to activity data aggregation server 106 during the activity (e.g., in real-time) and/or after the activity has been completed. In some embodiments, device 102 is configured to present an interactive user interface (e.g., through an activity tracking application executing at device 102). The user interface may display GPS data and receive selections (e.g., made by a user) with respect to the displays. In some embodiments, device 102 sends the selections that it receives to GAP modeling server 108.

In some embodiments, a user interface may be presented at device 102. In some embodiments, the user interface may be presented by GAP modeling server 108 through an associated activity tracking application executing at device 102 or by another component that is not shown in the example of FIG. 1. In some embodiments, the user interface is configured to show a visual output that is determined by GAP modeling server 108. In some embodiments, the visual output is determined based on the adjustment of the pace of a recorded (e.g., run) activity based on a GAP model that was generated by GAP modeling server 108. The user inputs and/or selections received at device 102 are configured to be sent to GAP modeling server 108.

Activity data aggregation server 106 is configured to aggregate recorded athletic activity data from devices such as device 102. In some embodiments, the activity data received at activity data aggregation server 106 is received during the activities (e.g., in real-time) and/or subsequent to the completion of the activities. Activity data aggregation server 106 is configured to store information associated with each activity. For example, information associated with each activity includes an identifier associated with the athlete that performed the activity, the activity type associated with the activity, the date and/or period of time during which the activity took place, the device type that was used to record the activity data, and the equipment used by the athlete during the activity. In some embodiments, the information associated with each activity may include attributes associated with the activity that were input by an athlete and/or attributes associated with the activity that were inferred from the recorded data. In some embodiments, the information associated with each activity is stored by activity data aggregation server 106 in an activity table that comprises an SQL database. Activity data aggregation server 106 is configured to store the set of GPS data (e.g., a set of GPS/Lat-Lng data points) and a corresponding auxiliary data (e.g., barometric/elevation data, timestamps, watts, heart rates, power, etc.) associated with (e.g., each recorded GPS data point along) each activity. In some embodiments, the set of GPS data and a corresponding set of auxiliary data associated with each activity are stored by activity data aggregation server 106 in a virtual hard drive (e.g., Amazon Simple Storage Service) associated with dynamically expanding storage availability. Activity data aggregation server 106 is configured to process the data received for each activity and perform spatial indexing for each activity based on the set of GPS data associated with the activity. In some embodiments, in performing spatial indexing, the information from the activity table and the GPS and corresponding auxiliary data from the virtual hard drive are put together and recorded for each recorded GPS data point and put into a PostGIS database or other spatially enabled and indexed data structure. Activity data aggregation server 106 is configured to send the aggregated activity data to GAP modeling server 108.

GAP modeling server 108 is configured to fit a GAP model using the recorded activity data. In some embodiments, GAP modeling server 108 is implementing using Apache Spark® (a distributed cluster computation framework that uses virtual machines running on Amazon Web Services®) and/or Apache Mesos® (a cluster manager). In various embodiments, GAP modeling server 108 is configured to obtain activities that are recorded by various users from activity data aggregation server 106. For example, the activities are associated with a selected activity type (e.g., running). In some embodiments, the obtained activities do not need to be recorded along the same or even similar geographic tracks (which are sometimes referred to as "segments" herein). GAP modeling server 108 is configured to filter at least some of obtained activity data out based on such activity data being associated with noisy GPS and/or auxiliary data such that activities with abnormal attributes are not used in the generation of a GAP model. In various embodiments, GAP modeling server 108 is configured to analyze for each athlete, based on the athlete's various heart rate values that are recorded along different points of activities performed by that athlete, a sample portion of the activities that are associated with higher heart rates. For example, GAP modeling server 108 is configured to identify a sample portion of activities that are associated with recorded heart rates that are within a range of percentile heart rates for that athlete. It is presumed that a higher heart rate is associated with the athlete expending more effort at that particular point in the activity (e.g., run). Details associated with generating the GAP model based on the selected portions are described in further detail below. The selected portions of the activities are used to fit a GAP model, which comprises a function that maps elevation gradient values (i.e., vertical elevation change per horizontal distance) to a dimensionless grade pace adjustment coefficient that gives the relative difficulty of running some pace at that elevation gradient versus running at zero gradient (i.e., on a flat elevation). In some embodiments, GAP modeling server 108 is configured to store the generated GAP model. In some embodiments, GAP modeling server 108 is configured to send a copy of the generated GAP model to devices such as device 102 for the devices to locally store.

GAP modeling server 108 is configured to adjust the recorded pace of a received activity (e.g., run) based on the generated GAP model. In some embodiments, the received activity is uploaded by a device such as device 102 and/or stored at activity data aggregating server 106 and includes a respective recorded/computed pace and measured/computed gradient with each of a series of recorded GPS data points. The pace is adjusted for each recorded GPS data point by multiplying the corresponding grade pace adjustment coefficient that corresponds to the respective measured/computed gradient with the recorded/computed pace associated with that GPS data point. As a result, the recorded/computed pace associated with each recorded GPS data point of the received activity is scaled by the corresponding grade pace adjustment coefficient that is indicated by the GAP model. The resulting, adjusted pace associated with each recorded GPS data point provides the pace that the athlete would have performed had he or she been running on a flat elevation (which is associated with a grade pace adjustment coefficient of one). In some embodiments, GAP modeling server 108 is configured to present a visualization of the recorded/computed pace along points of an activity along with another visualization of the adjusted pace along points of the same activity so that a viewer can see the comparison between the recorded/computed pace and the adjusted one.

As such, GAP modeling server 108 is configured to leverage millions of activities performed by tens and thousands of athletes to generate an accurate GAP model that can be used to adjust the pace of subsequently received activities.

A first example application of using a generated GAP model to adjust the recorded pace of a received activity is if an athlete (e.g., a runner) wants to train at a particular pace for running on a flat surface but may not find a flat surface to run on. But with the availability of the GAP model, the user can record a run on a surface that is not consistently flat and be able to convert the recorded pace of the run into a GAP to learn what his or her pace was had he or she been running on a flat surface. A second example application of using a generated GAP model to adjust the recorded pace of a received activity is allowing an athlete (e.g., a runner) to quantify how their hill running ability compares to their flat running ability. By seeing if their GAP is slower or faster than what they can achieve on flat pace, they can learn this.

Figure 2:
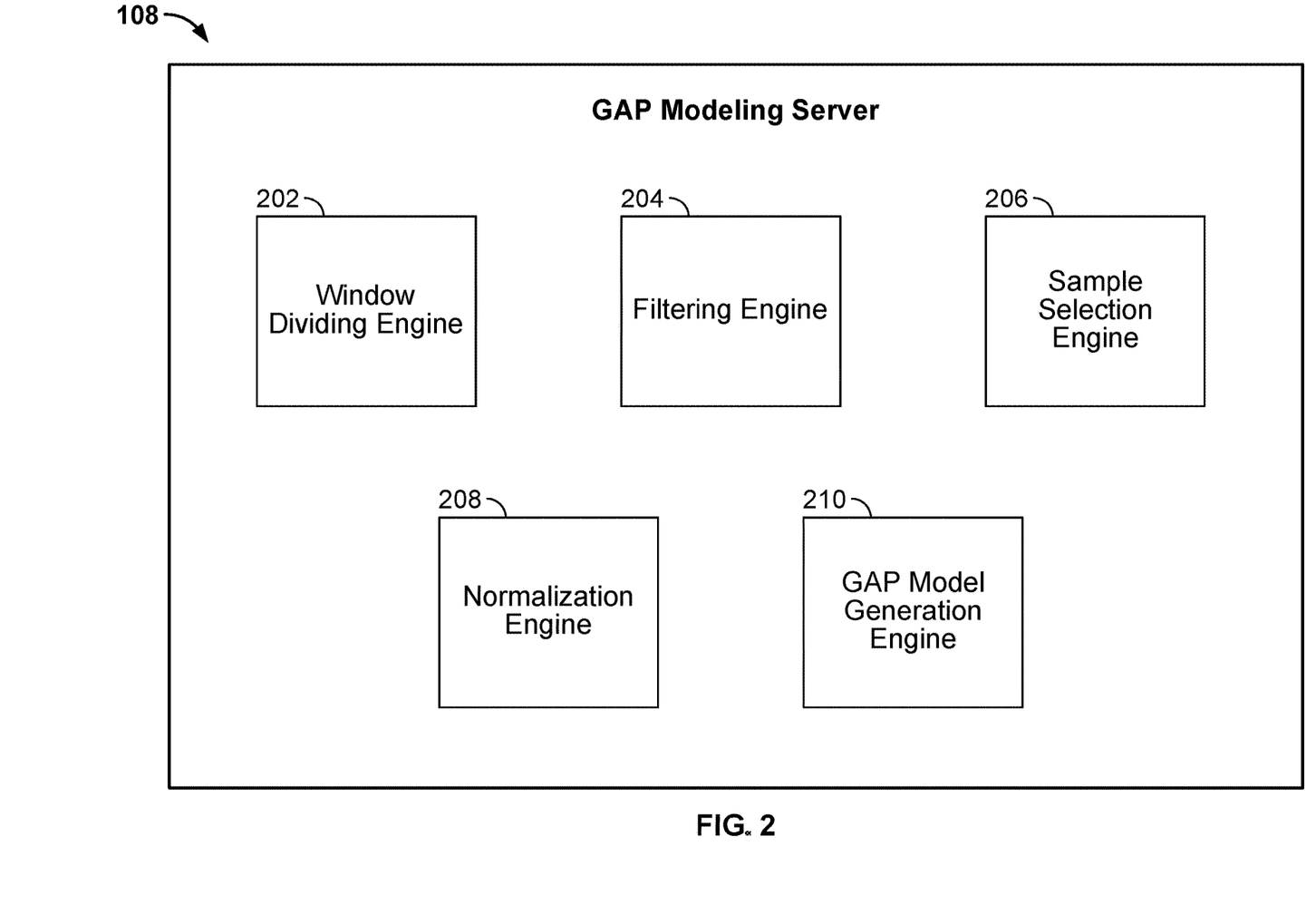
FIG. 2 is a diagram showing an example of a GAP modeling server in accordance with some embodiments.

FIG. 2 is a diagram showing an example of a GAP modeling server in accordance with some embodiments. In some embodiments, GAP modeling server 108 of FIG. 1 may be implemented using the example of FIG. 2. The example GAP modeling server includes window dividing engine 202, filtering engine 204, sample selection engine 206, normalization engine 208, and GAP model generation engine 210. In some embodiments, each of window dividing engine 202, filtering engine 204, sample selection engine 206, normalization engine 208, and GAP model generation engine 210 can be implemented, for example, as distinct or integrated software components, which can include module (s), package(s), and/or other distinct or integrated subcomponents to provide an executable computer program that can perform these described functions when executed on a processor, and can be implemented using a programming language such as Scala, Go, Java, Python, Objective C, and/or other programming languages. An example hardware computing environment to execute the components of FIG. 2 includes a cloud computing service, such as Amazon's Web Services®.

Window dividing engine 202 is configured to divide each activity into windows of data of a predetermined length of time. For example, each window includes two minutes worth of recorded activity data. The activities may belong to multiple athletes and have been recorded across different geographical tracks (segments). Each activity includes at least a series of recorded GPS data points, a corresponding timestamp for each GPS data point, a corresponding heart rate for each GPS data point, and a corresponding elevation for each GPS data point. The pace corresponding to each GPS data point is determined using the GPS and timestamp information. The gradient corresponding to each GPS data point is determined using the relative elevation information between GPS data points. For example, a recorded GPS data point includes a corresponding Latitude, Longitude, and Elevation. From this information associated with a recorded GPS data point, the gradient associated with the GPS data point can be determined, for example, as the local difference in elevation divided by the local distance in the Latitude/Longitude dimension relative to an adjacent GPS data point. For example, for a received activity, a distance stream, which is the elapsed distance in Latitude/Longitude traveled, and an elevation stream, which is the instantaneous elevation, are received. A similar calculation from those two streams to obtain the gradient elevation corresponding to each recorded GPS data point of the activity is performed.

Filtering engine 204 is configured to compute statistical measurements of one or more types of data that are associated with windows of activity data that had been divided by window dividing engine 202. For example, window dividing engine 202 is configured to determine the mean and standard deviation of the heart rate, gradient, and pace determined for the windows and those windows that meet outlier condition(s) (e.g., over three standard deviations away from the mean) are filtered out and not used to generate the GAP model. Put another way, the windows associated with noisy or anomalous data or with data indicative that the athlete was not in a steady state of activity (e.g., running) are excluded from further processing. The remaining windows of activity data are treated as single data points and the GAP model is fit over at least some of these data points that relate the mean gradient to the mean pace.

Sample selection engine 206 is configured to select a subset of windows of activity associated with each athlete. Because two different athletes might have totally different running efficiencies, and also have runs of different intensities, global averaging would produce a model with a very wide distribution. To reduce this uncertainty, in some embodiments, a filtering and a normalization step are applied to the windows associated with each athlete. For every athlete, in some embodiments, only windows from that athlete with a heart rate mean within a narrow range of a high percentile of that athlete's heart rate samples as determined from all available windows of data from them are considered. This ensures that the considered data represents hard to maximum efforts from that athlete and not a variety of efforts. For example, sample selection engine 206 is configured to select only windows of activity data associated with an athlete in which the mean heart rate across each window is within a predetermined percentile range of heart rate for that particular athlete. For example, sample selection engine 206 is configured to sort the windows for a particular athlete by their corresponding mean heart rate (e.g., the mean heart rate for a window is computed based on the one or more heart rate values that are included in the window). Then, sample selection engine 206 is configured to select the subset of windows whose mean heart rates are between the $70^{th}$ percentile to the $90^{th}$ percentile of mean heart rates for each athlete.

While the basis of selecting the subset of windows for an athlete is based only on heart rate in this example, in actual practice, the subset of windows can be selected for each athlete as a function of heart rate in addition to other athlete attributes such as age and weight, for example.

In some other embodiments, a subset of windows does not need to be selected for each athlete in the event that activities pertaining only to races are considered because it is assumed that there is high perceived effort for each athlete during races.

Normalization engine 208 is configured to determine, for each athlete, the "median pace near zero gradient" based on the subset of windows (e.g., the subset of windows that has been selected by sample selection engine 206 for being within the high percentile heart rate range of that athlete) that has been selected for that athlete. For example, a threshold gradient value (e.g., a small positive gradient value near zero) may be predetermined such that the one or more windows among the selected subset for each athlete for which the mean gradient is less than the threshold gradient value are identified. Then the median mean pace among the identified windows for each athlete is determined as the "median pace near zero gradient." Then normalization engine 208 is configured to normalize the mean pace of each window within the selected subset of windows that has been selected for each athlete based on the determined "median pace near zero gradient" for that same athlete.

In some other embodiments in which only activities that are performed in races are considered, each athlete's mean pace in windows near zero gradient (flat elevation) can be computed and the pace in all the windows may be normalized based on the mean pace.

GAP model generation engine 210 is configured to generate a GAP model based on the normalized mean pace of each window that has been part of the selected subset of windows across athletes. In some embodiments, GAP model generation engine 210 is configured to generate bins, where each bin is a range of gradient values. Different bins may include a different range of gradient values. For example, the width (range of gradients) of a bin may be determined based on the number of windows whose mean gradients match that bin. In some embodiments, GAP model generation engine 210 does not bin windows for which the mean gradient is near zero. GAP model generation engine 210 is configured to identify the windows whose corresponding mean gradient values match a bin and then determine the median (or some other statistical measurement) normalized mean pace of those windows. The median of the normalized mean pace of those windows that match each gradient bin then becomes the grade pace adjustment coefficient corresponding to that gradient bin. In some embodiments, GAP model generation engine 210 is configured to perform linear interpolation to connect together the grade pace adjustment coefficients corresponding to each gradient bin to generate a smooth GAP model that provides a grade pace adjustment coefficient for the pace measured/computed at each gradient. For example, the GAP model may be stored as an array of grade pace adjustment coefficients with corresponding gradient values.

In some embodiments, GAP model generation engine 210 is configured to receive a new activity, comprising at least pace information (computed or measured) and gradient information (computed or measured) corresponding to each recorded GPS data point. GAP model generation engine 210 is configured to adjust each pace value associated with the received activity by multiplying/scaling it by the corresponding grade adjustment coefficient of the generated GAP model corresponding to the corresponding gradient value.

Figure 3:
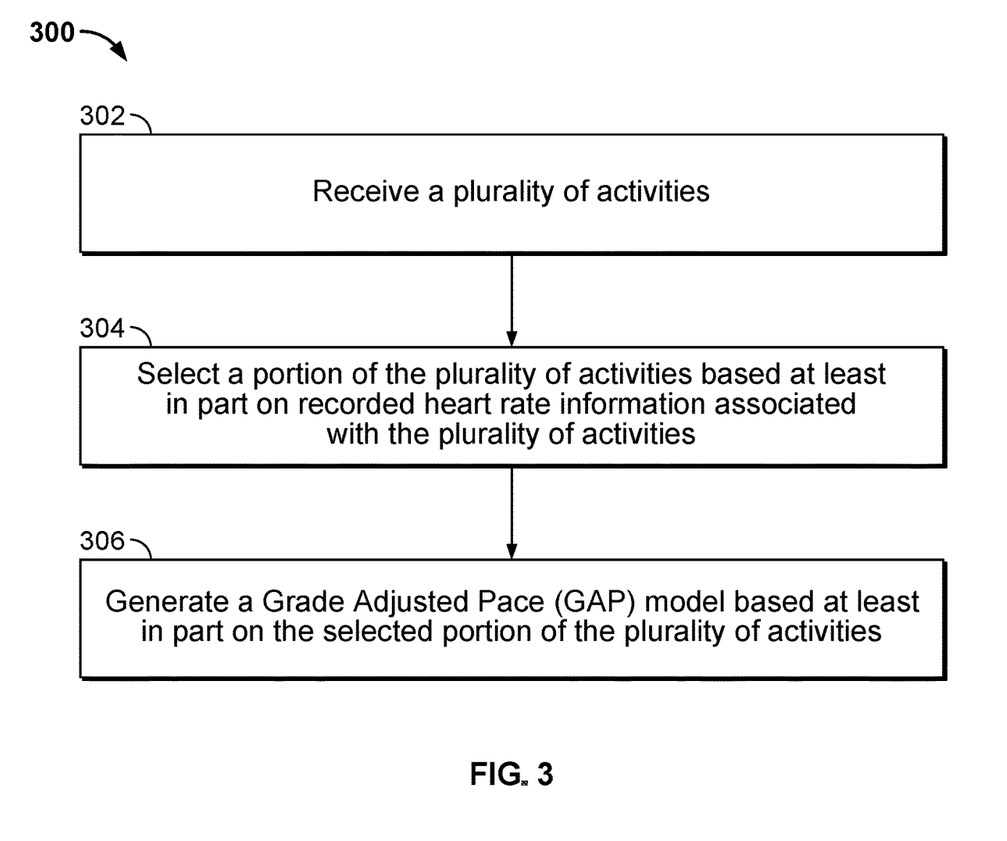
FIG. 3 is a flow diagram showing an embodiment of a process for using aggregate activity data to generate a Grade Adjusted Pace (GAP) model in accordance with some embodiments.

FIG. 3 is a flow diagram showing an embodiment of a process for using aggregate activity data to generate a Grade Adjusted Pace (GAP) model in accordance with some embodiments. In some embodiments, process 300 is implemented at GAP modeling server 108 of FIG. 1.

At 302, a plurality of activities is received. In some embodiments, all of the activities that are to be used to generate the GAP model are performed by one athlete. In some embodiments, the activities that are to be used to generate the GAP model are performed by various athletes.

At 304, a portion of the plurality of activities is selected based at least in part on recorded heart rate information associated with the plurality of activities. In some embodiments, for each athlete, at least a portion of the activities that have been recorded with a high range of mean heart rates for that athlete is selected and to be used to generate the GAP model. It is assumed that portions of activities that are associated with higher recorded heart rates (e.g., with heart rates that fall within a narrow range of percentile heart rates for that particular athlete) associated with the user are associated with higher expenditures of effort.

At 306, a Grade Adjusted Pace (GAP) model is generated based at least in part on the selected portion of the plurality of activities. The portions of activities that are associated with higher recorded heart rates and therefore, presumed greater efforts, are to be used to generate a GAP model.

Figure 4:
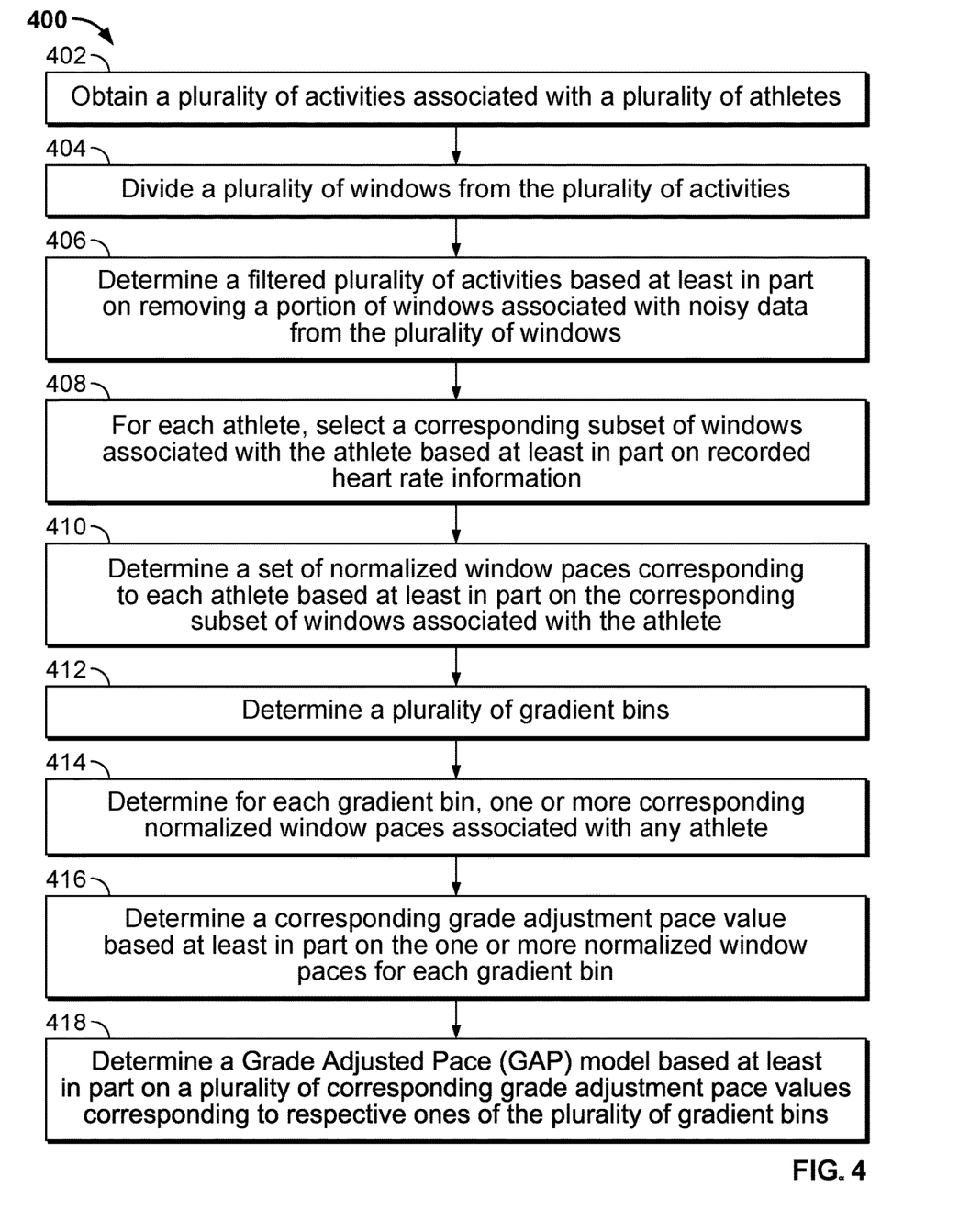
FIG. 4 is a flow diagram showing an example of a process for using aggregate activity data to generate a Grade Adjusted Pace (GAP) model in accordance with some embodiments.

FIG. 4 is a flow diagram showing an example of a process for using aggregate activity data to generate a Grade Adjusted Pace (GAP) model in accordance with some embodiments. In some embodiments, process 400 is implemented at GAP modeling server 108 of FIG. 1. In some embodiments, process 300 of FIG. 3 is implemented using the example of process 400.

At 402, a plurality of activities associated with a plurality of athletes is obtained. In various embodiments, the activities are associated with the same activity type. In various embodiments, the activities are running activities that are recorded by various athletes. In various embodiments, the activities could be recorded along similar or different geographic tracks (segments). In various embodiments, each activity comprises a series of recorded GPS data points and for each GPS data point, at least the following: a corresponding timestamp, a recorded heart rate, and a recorded elevation. The combination of GPS information and timestamp information can be used to derive a corresponding pace corresponding to each GPS data point of each activity. The elevation data corresponding to adjacent GPS data points can be used to derive an elevation gradient corresponding to each GPS data point of each activity.

In some embodiments, process 400 may be performed periodically using new or an updated set of activities obtained at 402 to ensure that the generated GAP model accurately reflects the most up-to-date or most recently available activity data.

At 404, a plurality of windows is divided from the plurality of activities. Each activity is divided into a series of windows where each window is of a predetermined length of time. For example, each time window is two minutes long. Each time window therefore includes one or more GPS data points and their corresponding pace, heart rate, and elevation gradient information.

At 406, a filtered plurality of activities is determined based at least in part on removing a portion of windows associated with noisy data from the plurality of windows. At least some of the windows of activity data are discarded (filtered out) if their corresponding (e.g., mean) pace, heart rate, and/or elevation gradient information appears to be anomalous or noisy. For example, the mean pace, the mean heart rate, and the mean elevation gradient may be computed and the standard deviation for pace, heart rate, and elevation gradient may be computed as well across all the activities obtained at step 402. Then, the windows of activity data with the mean pace, the mean heart rate, and the mean elevation gradient that are a predetermined number of standard deviations away from the mean pace, the mean heart rate, and the mean elevation gradient across all the activities are filtered out or otherwise ignored in generating the GAP model.

At 408, for each athlete, a corresponding subset of windows associated with the athlete is selected based at least in part on recorded heart rate information. In various embodiments, for each athlete, a subset of windows of activity is selected based at least on the windows' mean heart rate information. For example, the subset of windows of activity data are selected because they have mean heart rates for a given athlete that are relatively higher than the mean heart rates of other windows of activity data associated with the same athlete. The reason that windows with relatively higher mean heart rates are selected is that it is believed that the heart rates indicate a higher expenditure of effort. Samples of activities that are associated with higher heart rates or other indications of higher expenditures of effort are used in some embodiments because it is presumed that activities that are to be adjusted using a generated GAP model will be associated with high perceived efforts. Only these selected subsets of windows of activity data that have been selected for corresponding athletes are used to generate the GAP model while windows of activity data that are not selected for each athlete are not used to generate the GAP model.

For example, windows of activity data are grouped together by athlete. The windows of activity data associated with the same athlete are ordered by their respective mean heart rates. Those windows within a predetermined narrow range of percentile heart rate (e.g., $70^{th}$ to $90^{th}$ percentile) are selected for that athlete.

In some embodiments, the subset of windows can be selected for each athlete as a function of the mean heart rate of the windows and also the athlete's age. For example, an athlete's age can be used to determine which range of mean heart rates for which corresponding windows of activity data are to be selected for that athlete.

Figure 5:
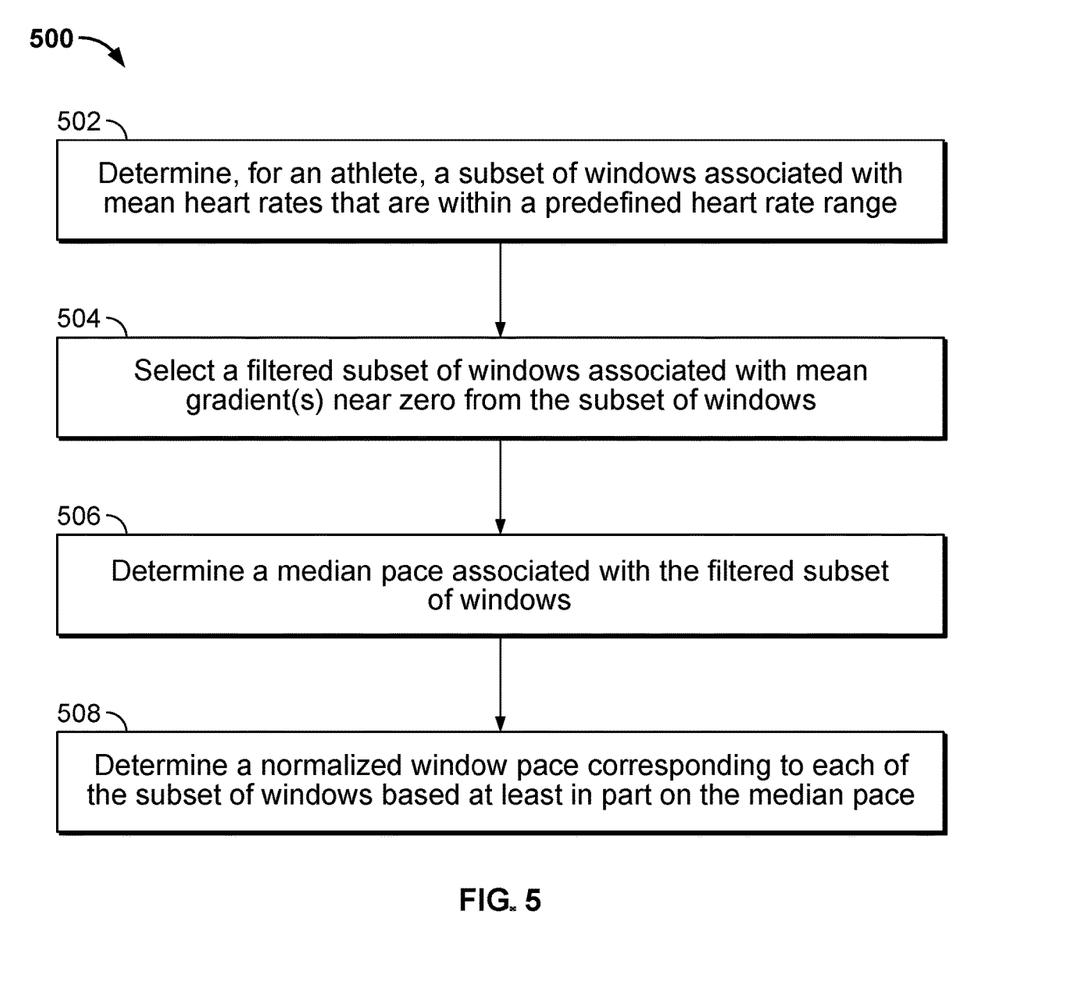
FIG. 5 is a flow diagram showing an example of a process for determining a set of normalized window paces corresponding to each athlete in accordance with some embodiments.

At 410, a set of normalized window paces corresponding to each athlete is determined based at least in part on the corresponding subset of windows associated with the athlete. In some embodiments, the mean pace of each window that is within the selected subset for an athlete is normalized. In some embodiments, the mean pace of each window that is within the selected subset for an athlete is normalized based on a value that is derived from the windows of activity data that have been selected for that athlete. For example, this value is referred to as the "median pace near zero gradient" and is determined for each athlete based on the windows of activity data that have been selected for that athlete. FIG. 5, below, describes an example process of normalizing the mean pace of each window that is within the selected subset for each athlete using the "median pace near zero gradient" that is determined for that athlete. In some embodiments, the normalized pace of each window within the selected subset of windows for an athlete is referred to as a "normalized window pace."

At 412, a plurality of gradient bins is determined. In some embodiments, each gradient bin is a range of elevation gradients. In some embodiments, the range of gradients for each bin is fixed. In some embodiments, the range of gradients for each bin is variable and dependent upon the number of windows whose corresponding mean gradient matches that bin, as will be described with step 414, below. For example, wherein the range of gradients for a bin is variable, the range of gradients may be increased until the corresponding mean gradients corresponding to at least a predetermined number of windows match the range of gradients for that bin.

Normalization was performed for each athlete at step 410, above, because without normalization, the variance in each gradient bin of step 412 would be as large as the variance of actual athletes (e.g., runners). For example, one runner might be twice as fast as another. If they both had a window pace sample in the same gradient bin, then the average within that bin would have to be determined. Normalization removes this component of variation of individual runner speed, while keeping the component of variation due to differing gradients.

At 414, for each gradient bin, one or more corresponding normalized window paces associated with any athlete are determined. For each gradient bin, the windows of activity data that are within the selected subsets (at step 408, above) for any athlete whose corresponding mean gradient matches the gradient range of that bin are determined. As such, for each gradient bin, there is a set of normalized window paces corresponding to the set of windows, across all athletes, whose corresponding mean gradients match the gradient range of that bin.

At 416, a corresponding grade adjustment pace value is determined based at least in part on the one or more normalized window paces for each gradient bin. In some embodiments, the median of all the set of normalized window paces corresponding to a gradient bin is determined as the corresponding grade adjustment pace value/coefficient corresponding to that gradient bin.

At 418, a Grade Adjusted Pace (GAP) model is determined based at least in part on a plurality of corresponding grade adjustment pace values corresponding to respective ones of the plurality of gradient bins. A GAP model is determined from all the grade adjustment pace values/coefficients corresponding to respective ones of the gradient bins. For example, the corresponding grade adjustment pace values could be strung together to form a continuous GAP model. In some embodiments, the GAP model is stored as an array of value pairs where each pair comprises a gradient bin and a corresponding grade adjustment value/coefficient. The GAP model represents the relationship between gradient to normalized activity (e.g., running) pace.

FIG. 5 is a flow diagram showing an example of a process for determining a set of normalized window paces corresponding to each athlete in accordance with some embodiments. In some embodiments, process 500 is implemented at GAP modeling server 108 of FIG. 1. In some embodiments, steps 408 and 410 of process 400 of FIG. 4 are implemented using the example of process 500.

An instance of process 500 may be performed for each athlete to determine normalized window paces for that athlete.

At 502, a subset of windows associated with mean heart rates that are within a predefined heart rate range is determined for an athlete. In some embodiments, the subset of windows of activity data associated with an athlete and that are associated with a higher range of heart rates for that particular athlete is selected. As mentioned above, for example, the windows of activity data associated with an athlete may be ordered by their respective mean heart rates. Then, those windows that are within a predetermined narrow percentile heart rate range (e.g., $70^{th}$ to $90^{th}$ percentile) may be selected.

At 504, a filtered subset of windows associated with mean gradient(s) near zero is selected from the subset of windows. Of the selected subset of windows, those windows within a mean elevation gradient that is near zero are determined. For example, an elevation threshold value (e.g., a positive but low gradient value) can be set such that windows with corresponding mean elevation gradients less than the elevation threshold value are determined to be "near zero gradients."

At 506, a median pace associated with the filtered subset of windows is determined. The median pace is then determined among those windows that have corresponding mean elevation gradients that are determined to be "near zero gradients."

At 508, a normalized window pace corresponding to each of the subset of windows is determined based at least in part on the median pace. The mean pace of each window of the subset selected at step 502 is divided by the median pace determined at step 506 among the windows to be near zero gradient to determine a normalized window pace for each window.

Figure 6:
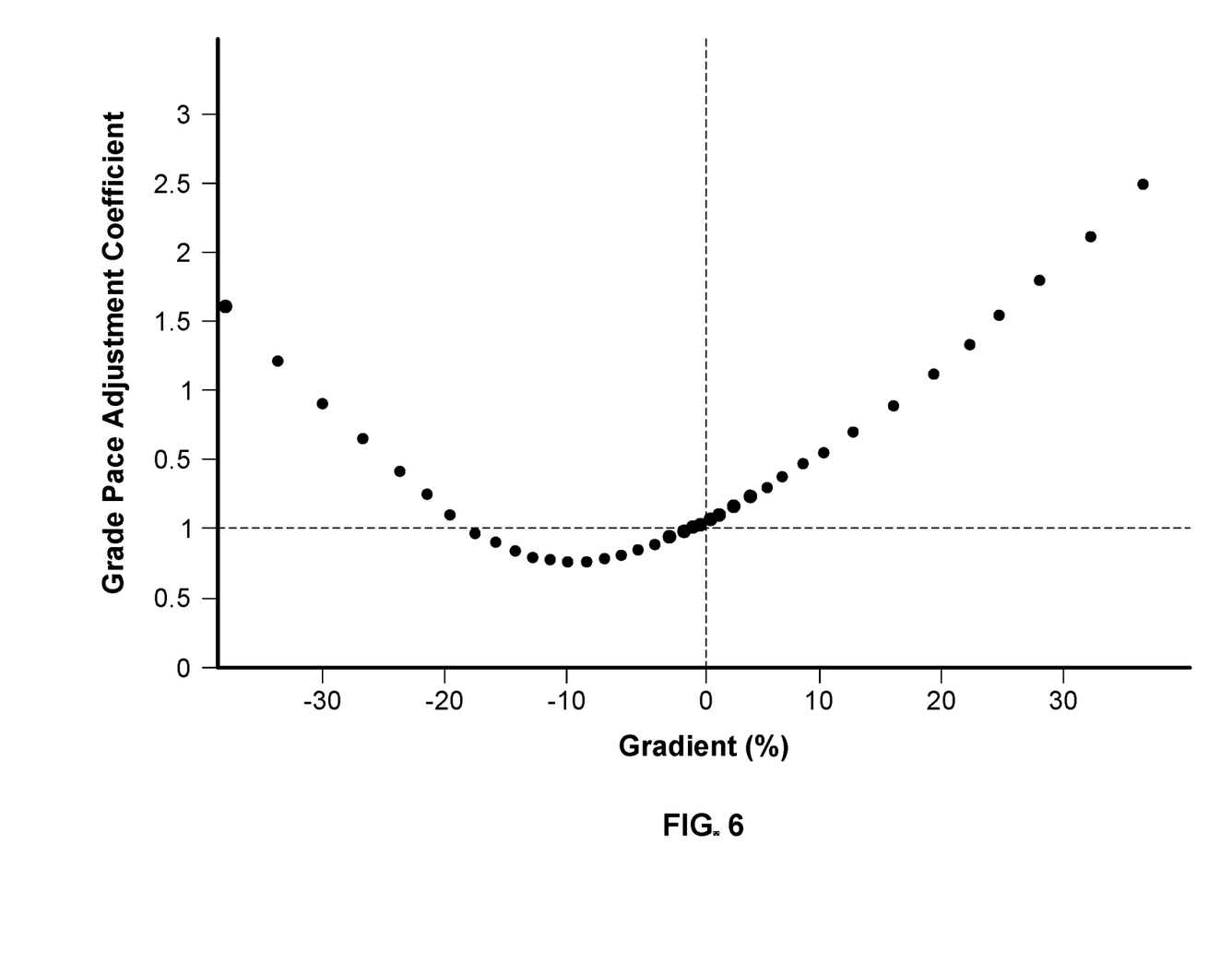
FIG. 6 is a diagram showing an example of a plot of a generated GAP model in accordance with some embodiments.

FIG. 6 is a diagram showing an example of a plot of a generated GAP model in accordance with some embodiments. In the example, the determined grade pace adjustment coefficients are plotted on the vertical axis against the elevation gradients on the horizontal axis. For example, grade pace adjustment coefficients are determined using a process such as process 300 of FIG. 3 or process 400 of FIG. 4. The curve of the example GAP model shows that paces recorded at gradients of a relatively higher magnitude (e.g., −30% or 30%) are to be adjusted with a greater grade pace adjustment coefficient to account for the greater effort that it takes to perform an activity (e.g., running) at those degrees of incline or decline on the surface on which the activity is performed. Furthermore, the example GAP model shows that paces recorded at or near zero gradient need not be adjusted significantly (i.e., those recorded paces would be multiplied by a grade adjustment pace coefficient of one or a value close to one). The example GAP model also shows that when paces are recorded at a slight decline (i.e., a negative gradient that is lower in magnitude such as the range between −18% and 0%), the adjusted pace can be reduced (i.e., multiplied by a positive value that is less than one) to account for the fact that running on a slight decline requires less effort than running on a flat surface (i.e., at zero gradient), unlike running down a greater decline, which requires more effort than running on a flat surface.

Figure 7:
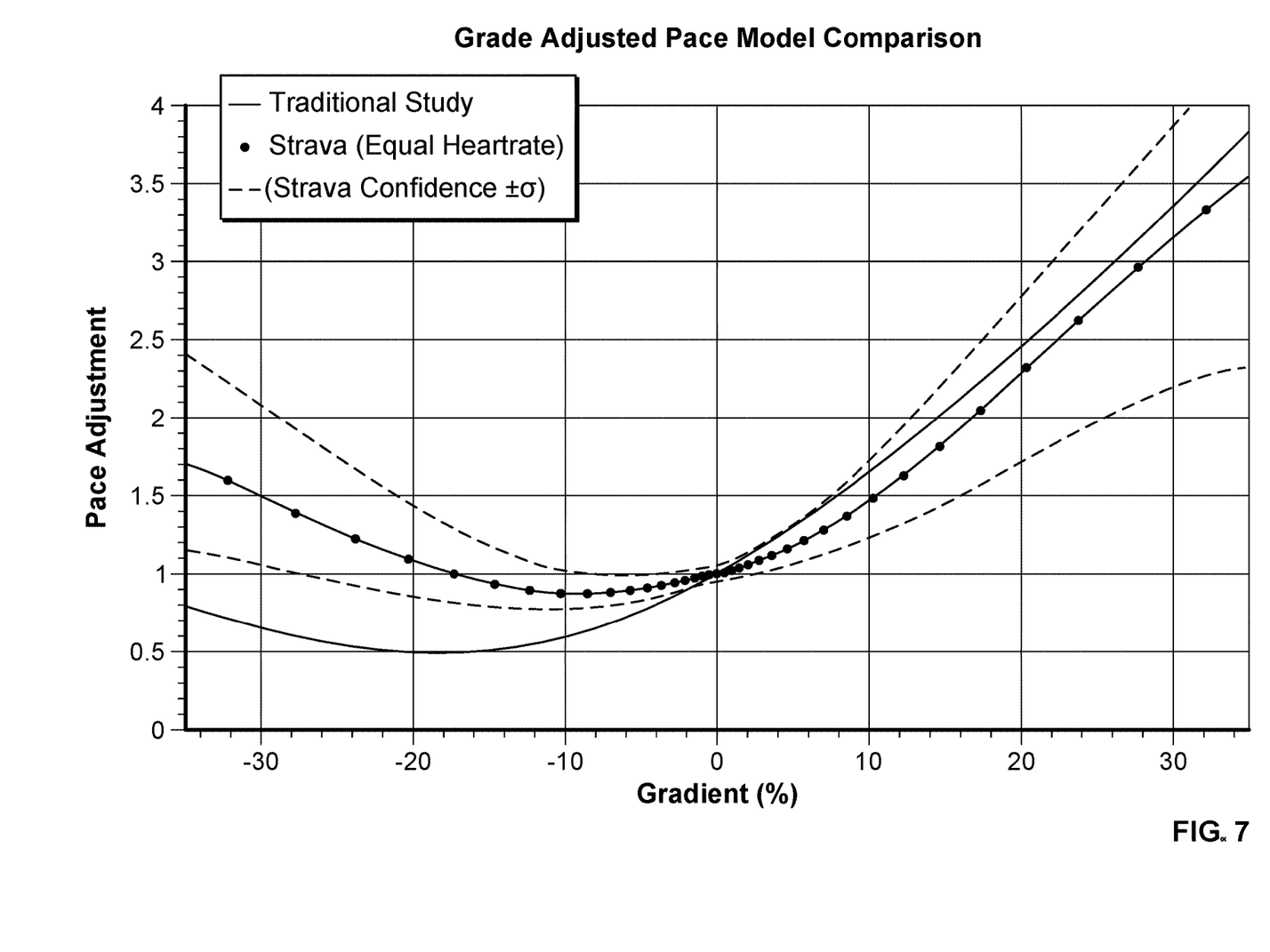
FIG. 7 is a diagram showing a plot of a generated GAP model generated in accordance with some embodiments and a GAP model that is generated using a traditional study of athletes in a lab setting.

FIG. 7 is a diagram showing a plot of a generated GAP model generated in accordance with some embodiments and a GAP model that is generated using a traditional study of athletes in a lab setting. The example plots show a GAP model that is shown in a continuous line (labeled as "Traditional study" in the diagram) that is determined using a traditional study of athletes in a lab setting (e.g., running on a treadmill). The example plots also show a GAP model that is shown as a linear interpolation of discrete grade adjustment pace coefficients (labeled as "Traditional study" in the diagram) generated using aggregate activity data in accordance with some embodiments. The two plots differ in at least that the GAP model generated by the traditional study errs in predicting the pace adjustment needed for when there is a greater decline (e.g., greater negative gradient) by presuming that less effort is needed to be expended at the greater decline, when in fact, more effort is needed to perform an activity at the greater decline.

Figure 8:
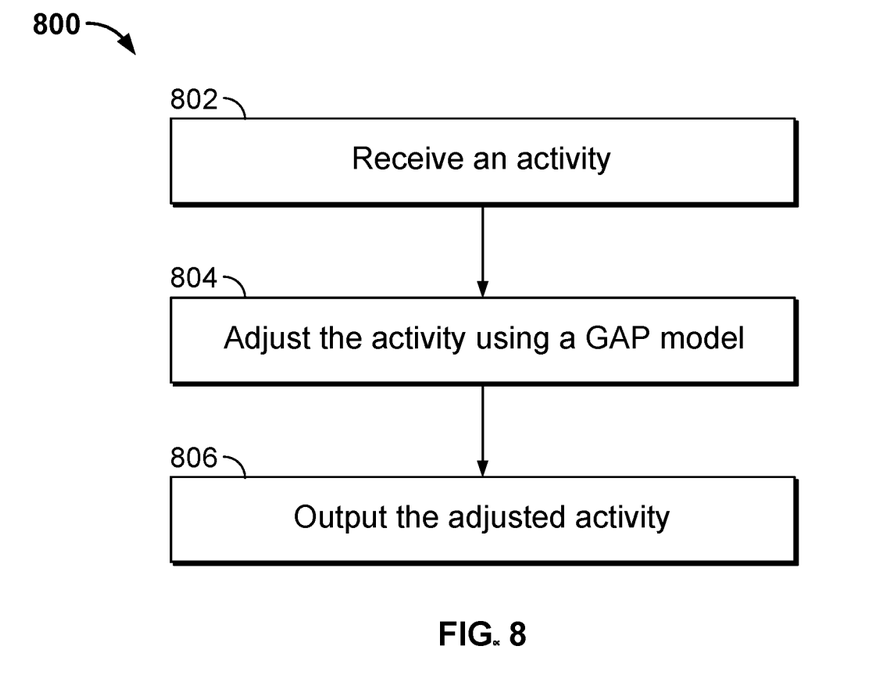
FIG. 8 is a flow diagram showing an embodiment of a process for adjusting an activity using a GAP model in accordance with some embodiments.

FIG. 8 is a flow diagram showing an embodiment of a process for adjusting an activity using a GAP model in accordance with some embodiments. In some embodiments, process 800 is implemented at GAP modeling server 108 of FIG. 1.

At 802, an activity is received. A recorded activity is received. In various embodiments, the activity comprises a series of GPS data points and for each GPS data point, a corresponding timestamp, a corresponding recorded heart rate, and a corresponding recorded elevation. A recorded pace is determined for each GPS data point based at least in part on the recorded GPS information and recorded timestamp information. An elevation gradient is determined for each GPS data point based at least in part on the recorded elevations of adjacent GPS data points.

At 804, the activity is adjusted using a GAP model. In some embodiments, each recorded pace of the activity is adjusted based on the grade adjustment pace coefficient associated with the corresponding elevation gradient at the recorded pace in the activity. For example, the recorded pace is multiplied by the grade adjustment pace coefficient in the GAP model that matches the elevation gradient associated with the surface at which the recorded pace was recorded. Specifically, referring to the example GAP model shown in FIG. 6, if the recorded pace were 10 minutes/mile at the gradient of 10%, the corresponding grade adjustment pace coefficient would be approximately 0.5, and therefore the adjusted pace would be 0.5×10 minutes/mile=5 minutes/mile.

At 806, the adjusted activity is output. In some embodiments, the adjusted paces of the activity can be plotted against the distance of the activity (e.g., run). In some embodiments, the adjusted paces of the activity can be plotted against the distance of the activity in a presentation. In some embodiments, the adjusted paces of the activity can be plotted against the distance of the activity and in the same presentation, the elevation gradient at each distance can also be displayed. In some embodiments, the adjusted paces of the activity can be plotted against the distance of the activity along with the pre-adjustment paces of the activity against the distance of the activity to contrast the pace of the activity in a presentation, with and without adjustment based on elevation gradient. In some embodiments, the average grade adjusted pace can be determined for an activity and presented. For example, for a run at 9 minutes/mile pace up a hill of uniform gradient, the average grade adjusted is 7 minutes/mile.

Figure 9:
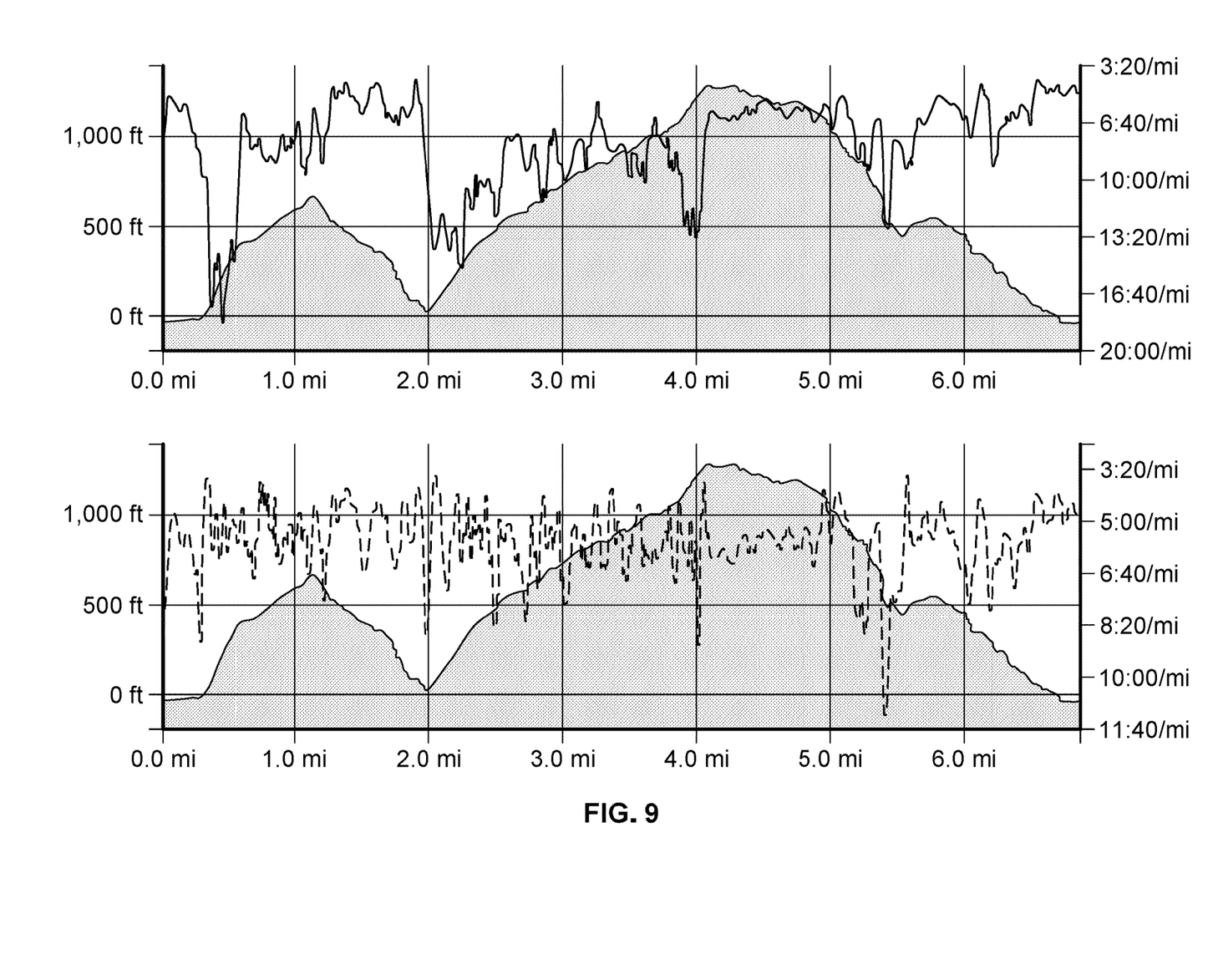
FIG. 9 is a diagram showing two plots related to the same example run.

FIG. 9 is a diagram showing two plots related to the same example run. The top plot shows the actual recorded running pace plotted against the distance of the run. The bottom plot shows the grade adjusted paces of the same run using a GAP model plotted against the distance of the run. Furthermore, both plots overlay the recorded elevation gradients of the run across the distance of the run. The run is from a very hilly race where the athlete is running at near maximum speed. As shown in the bottom plot, the grade adjusted paces of the run are much more uniform than the recorded pace.

Other variables besides gradient can affect the difficulty of running. That is, the examples of generating a GAP model produce a correction coefficient that is only a function of elevation gradient. Extensions to the model could be parameterized by other variables as well. One extension of the model could characterize the relative intensity for each athlete of every window of running data. The model then could be parameterized by a dimension of relative effort, from zero effort to maximum effort. One way to do this is via heart rate, for example. The model could be fitted against gradient and normalized heart rate.

Another dimension is duration of the activity. A GAP model could be fit to elevation gradient and the total length of the hill/descent. A more advanced model could characterize this function and would have to consider a run in its entirety along with its elevation profile, rather than only operating on a slice of time from the run.

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:

1. A system, comprising:
a memory; and
a processor coupled to the memory and configured to:
receive, from a plurality of devices enabled to record location information and elevation information, a plurality of activities associated with a plurality of athletes;
select a portion of the plurality of activities based at least in part on recorded heart rate information associated with the plurality of activities, including to:
divide the plurality of activities into a plurality of windows, wherein each window comprises recorded GPS data points that were recorded within a predetermined length of time; and
for each athlete, select a corresponding subset of windows associated with that athlete based at least in part on the corresponding subset of windows associated with that athlete meeting a predetermined percentile range of heart rate associated with that athlete;
generate a Grade Adjusted Pace (GAP) model based at least in part on the selected portion of the plurality of activities;
receive, from a first device, an activity comprising a plurality of GPS data points;
adjust the activity using the GAP model, including to adjust a respective pace corresponding to a GPS data point of the plurality of GPS data points based at least in part on a GAP coefficient associated with a corresponding elevation associated with that GPS data point; and
output, at a user interface of the first device, a visualization associated with the adjusted activity, including to:
output adjusted respective paces corresponding to the plurality of GPS data points in the visualization;
output non-adjusted respective paces corresponding to the plurality of GPS data points in the visualization; and
wherein the output of the adjusted respective paces and the non-adjusted respective paces are overlaid over recorded elevation gradients corresponding to the plurality of GPS data points.

2. The system of claim 1, wherein the activity comprises one or more of the following: geographic data, elevation data, time data, and heart rate data.

3. The system of claim 1, wherein the plurality of activities comprises a plurality of running activities.

4. The system of claim 1, wherein the portion of the plurality of activities comprises a first portion, wherein prior to selecting the first portion of the plurality of activities based at least in part on the recorded heart rate information associated with the plurality of activities, the processor is configured to filter out a second portion of the plurality of activities, wherein the second portion is associated with anomalous or noisy activity data.

5. The system of claim 1, wherein the processor is further configured to:
- determine a filtered plurality of activities based at least in part on removing a portion of windows associated with noisy or anomalous data from the plurality of windows;
- determine a set of normalized window paces corresponding to that athlete based at least in part on the corresponding subset of windows associated with that athlete;
- determine a plurality of gradient bins;
- determine for each gradient bin, one or more corresponding normalized window paces associated with any athlete; and
- determine a corresponding grade adjustment pace value based at least in part on the one or more corresponding normalized window paces for each gradient bin, wherein the GAP model is determined based at least in part on a plurality of corresponding grade adjustment pace values corresponding to respective ones of the plurality of gradient bins.

6. The system of claim 1, wherein for each athlete, to select the corresponding subset of windows associated with that athlete comprises to:
- order windows of activity data associated with that athlete based on the recorded heart rate information; and
- select from the ordered windows of activity data the corresponding subset of windows that is associated with the predetermined percentile range of heart rate associated with that athlete.

7. The system of claim 5, wherein to determine the set of normalized window paces corresponding to that athlete based at least in part on the corresponding subset of windows associated with that athlete comprises to:
- select a filtered subset of windows associated with mean gradient(s) near zero from the corresponding subset of windows;
- determine a median pace near zero gradient associated with the filtered subset of windows; and
- determine a normalized window pace corresponding to each of the corresponding subset of windows based at least in part on the median pace near zero gradient.

8. A method, comprising:
- receiving, from a plurality of devices enabled to record location information and elevation information, a plurality of activities associated with a plurality of athletes;
- selecting a portion of the plurality of activities based at least in part on recorded heart rate information associated with the plurality of activities, including:
  - dividing the plurality of activities into a plurality of windows, wherein each window comprises recorded GPS data points that were recorded within a predetermined length of time; and
  - for each athlete, selecting a corresponding subset of windows associated with that athlete based at least in part on the corresponding subset of windows associated with that athlete meeting a predetermined percentile range of heart rate associated with that athlete;
- generating a Grade Adjusted Pace (GAP) model based at least in part on the selected portion of the plurality of activities;
- receiving, from a first device, an activity comprising a plurality of GPS data points;
- adjusting the activity using the GAP model, including:
  - adjusting a respective pace corresponding to a GPS data point of the plurality of GPS data points based at least in part on a GAP coefficient associated with a corresponding elevation associated with that GPS data point; and
- outputting, at a user interface of the first device, a visualization associated with the adjusted activity, including:
  - outputting adjusted respective paces corresponding to the plurality of GPS data points in the visualization;
  - outputting non-adjusted respective paces corresponding to the plurality of GPS data points in the visualization; and
  - wherein the outputting of the adjusted respective paces and the non-adjusted respective paces are overlaid over recorded elevation gradients corresponding to the plurality of GPS data points.

9. The method of claim 8, wherein the activity comprises one or more of the following: geographic data, elevation data, time data, and heart rate data.

10. The method of claim 8, wherein the plurality of activities comprises a plurality of running activities.

11. The method of claim 8, wherein the portion of the plurality of activities comprises a first portion, wherein prior to selecting the first portion of the plurality of activities based at least in part on the recorded heart rate information associated with the plurality of activities, the method further comprises filtering out a second portion of the plurality of activities, wherein the second portion is associated with anomalous or noisy activity data.

12. The method of claim 8, further comprising:
- determining a filtered plurality of activities based at least in part on removing a portion of windows associated with noisy or anomalous data from the plurality of windows;
- determining a set of normalized window paces corresponding to that athlete based at least in part on the corresponding subset of windows associated with that athlete;
- determining a plurality of gradient bins;
- determining for each gradient bin, one or more corresponding normalized window paces associated with any athlete; and
- determining a corresponding grade adjustment pace value based at least in part on the one or more corresponding normalized window paces for each gradient bin, wherein the GAP model is determined based at least in part on a plurality of corresponding grade adjustment pace values corresponding to respective ones of the plurality of gradient bins.

13. The method of claim 8, wherein for each athlete, selecting the corresponding subset of windows associated with that athlete comprises:
- ordering windows of activity data associated with that athlete based on the recorded heart rate information; and
- selecting from the ordered windows of activity data the corresponding subset of windows that is associated with the predetermined range of percentile heart rates associated with that athlete.

14. The method of claim 12, wherein determining the set of normalized window paces corresponding to that athlete based at least in part on the corresponding subset of windows associated with that athlete comprises:
- selecting a filtered subset of windows associated with mean gradient(s) near zero from the corresponding subset of windows;
- determining a median pace near zero gradient associated with the filtered subset of windows; and determining a normalized window pace corresponding to each of the corresponding subset of windows based at least in part on the median pace near zero gradient.

15. A computer program product, the computer program product being embodied in a non-transitory computer readable storage medium and comprising computer instructions for:
- receiving, from a plurality of devices enabled to record location information and elevation information, a plurality of activities associated with a plurality of athletes;
- selecting a portion of the plurality of activities based at least in part on recorded heart rate information associated with the plurality of activities, including:
  - dividing the plurality of activities into a plurality of windows, wherein each window comprises recorded GPS data points that were recorded within a predetermined length of time; and
  - for each athlete, selecting a corresponding subset of windows associated with that athlete based at least in part on the corresponding subset of windows associated with that athlete meeting a predetermined percentile range of heart rate associated with that athlete;
- generating a Grade Adjusted Pace (GAP) model based at least in part on the selected portion of the plurality of activities;
- receiving, from a first device, an activity comprising a plurality of GPS data points;
- adjusting the activity using the GAP model, including adjusting a respective pace corresponding to a GPS data point of the plurality of GPS data points based at least in part on a GAP coefficient associated with a corresponding elevation associated with that GPS data point; and
- outputting, at a user interface of the first device, a visualization associated with the adjusted activity, including:
  - outputting adjusted respective paces corresponding to the plurality of GPS data points in the visualization;
  - outputting non-adjusted respective paces corresponding to the plurality of GPS data points in the visualization; and
  - wherein the outputting of the adjusted respective paces and the non-adjusted respective paces are overlaid over recorded elevation gradients corresponding to the plurality of GPS data points.

16. The computer program product of claim 15, wherein the portion of the plurality of activities comprises a first portion, wherein prior to selecting the first portion of the plurality of activities based at least in part on the recorded heart rate information associated with the plurality of activities, further comprising filtering out a second portion of the plurality of activities, wherein the second portion is associated with anomalous or noisy activity data.

* * * * *